(12) United States Patent
Kang et al.

(10) Patent No.: US 11,684,581 B2
(45) Date of Patent: Jun. 27, 2023

(54) DRUG AND LAYERED SILICATE COMPOSITE WITH IMPROVED ORAL BIOAVAILABILITY, ORAL PHARMACOLOGICAL COMPOSITION CONTAINING THE COMPOSITE AND METHOD FOR PRODUCING THE COMPOSITE

(71) Applicant: KOREA INSTITUTE OF GEOSCIENCE AND MINERAL RESOURCES, Daejeon (KR)

(72) Inventors: Il Mo Kang, Seoul (KR); Dae Duk Kim, Seoul (KR); Ju Hwan Park, Seoul (KR); Ki Min Roh, Daejeon (KR); Jangik Ike Lee, Seoul (KR); Jae Hwan Kim, Pohang-si (KR); Sung Man Seo, Pohang-si (KR); Su Young Jung, Seoul (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 0 days.

(21) Appl. No.: 16/295,051

(22) Filed: Mar. 7, 2019

(65) Prior Publication Data
US 2019/0274963 A1     Sep. 12, 2019

(30) Foreign Application Priority Data
Jan. 12, 2018 (KR) .................. 10-2018-0004449

(51) Int. Cl.
*A61K 9/48* (2006.01)
*A61K 9/14* (2006.01)
(Continued)

(52) U.S. Cl.
CPC ............ *A61K 9/4808* (2013.01); *A61K 9/143* (2013.01); *A61K 9/19* (2013.01); *A61K 9/485* (2013.01); *A61K 31/44* (2013.01); *A61K 47/6923* (2017.08)

(58) Field of Classification Search
CPC .. A61K 2300/00; A61K 45/06; A61K 31/505; A61K 31/27; A61K 31/44;
(Continued)

(56) References Cited

U.S. PATENT DOCUMENTS

2006/0013877 A1*  1/2006  Park .................... A61K 31/496
                                                424/484
2008/0119519 A1   5/2008  Choy et al.
(Continued)

FOREIGN PATENT DOCUMENTS

JP    2001-278810    10/2001
JP    2008-530205     8/2008
(Continued)

OTHER PUBLICATIONS

JPO, Office Action of JP 2020-534273 dated Jun. 15, 2021.
(Continued)

*Primary Examiner* — Bethany P Barham
*Assistant Examiner* — Ayaan A Alam
(74) *Attorney, Agent, or Firm* — Lex IP Meister, PLLC (57) ABSTRACT

A drug and layered silicate composite is provided. The drug and layered silicate contains layered silicate powders and a drug compound bound to between layers of the silicate powders, wherein the drug compound is present in an amorphous state in the composite. Using such a composite may significantly improve absorption and bioavailability of a sorafenib compound.

4 Claims, 7 Drawing Sheets

(51) Int. Cl.
*A61K 47/69* (2017.01)
*A61K 9/19* (2006.01)
*A61K 31/44* (2006.01)

(58) Field of Classification Search
CPC ...... A61K 33/00; A61K 31/35; A61K 31/366;
A61K 31/405; A61K 31/435; A61K
31/47; A61K 31/70; A61K 31/397; A61K
31/575; A61K 31/60; A61K 31/519;
A61K 31/19; A61K 9/4858; A61K
31/5377; A61K 31/685; A61K 47/38;
A61K 8/66; A61K 9/0019; A61K 9/2018;
A61K 31/661; A61K 8/0204; A61K
9/4808; A61K 9/485; A61K 9/4866;
A61K 2800/86; A61K 31/495; A61K
31/506; A61K 47/26; A61K 8/40; A61K
8/42; A61K 8/44; A61K 8/4973; A61K
9/00; A61K 9/0053; A61K 9/2013; A61K
9/2054; A61K 9/2059; A61K 9/4875;
A61K 9/4891; A61K 2800/70; A61K
31/404; A61K 31/436; A61K 31/4545;
A61K 31/4985; A61K 31/585; A61K
47/02; A61K 47/10; A61K 8/0216; A61K
8/64; A61K 9/0014; A61K 2800/412;
A61K 2800/522; A61K 2800/524; A61K
31/325; A61K 31/5395; A61K 38/00;
A61K 8/0208; A61K 8/445; A61K 8/60;
A61K 9/0043; A61K 9/0048; A61K
9/0078; A61K 9/06; A61K 9/19; A61K
2800/10; A61K 2800/413; A61K 2800/57;
A61K 2800/85; A61K 2800/92; A61K
31/05; A61K 31/12; A61K 31/165; A61K
31/196; A61K 31/222; A61K 31/255;
A61K 31/34; A61K 31/445; A61K
31/695; A61K 33/06; A61K 33/12; A61K
35/02; A61K 36/9066; A61K 47/58;
A61K 47/6923; A61K 8/11; A61K 8/14;
A61K 8/347; A61K 8/37; A61K 8/375;
A61K 8/46; A61K 8/466; A61K 8/4926;
A61K 8/494; A61K 8/4966; A61K 8/498;
A61K 8/553; A61K 8/671; A61K 8/676;
A61K 9/0024; A61K 9/0034; A61K
9/0085; A61K 9/143; A61K 9/146; A61K
9/51; A61K 9/5138; A61K 9/5153; A61K
9/70; A61K 9/7007
See application file for complete search history.

(56) References Cited

U.S. PATENT DOCUMENTS

2008/0213374 A1    9/2008  Carty et al.
2010/0272769 A1*  10/2010  Darlington, Jr. ....... A61K 33/12
                                                        424/409
2017/0143715 A1*   5/2017  Brisander ............ A61K 31/506

FOREIGN PATENT DOCUMENTS

| JP | 2009-543797 | 12/2009 |
| KR | 10-2004-0010306 | 1/2004 |
| KR | 10-2018-0002977 | 1/2018 |
| WO | 2005/018679 | 3/2005 |

OTHER PUBLICATIONS

Min-Soo Kim, "Soluplus-coated colloidal silica nanomatrix system for enhanced supersaturation and oral absorption of poorly water-soluble drugs", Artificial Cells, Nanomedicine and Biotechnology, vol. 41, No. 6, pp. 363-367, Dec. 1, 2013.

Xue-Qing Wang et al., "Bioavailability and pharmacokinetics of sorafenib suspension, nanoparticles and nanomatrix for oral administration to rat", International Journal of Pharmaceutics, Elsevier, NL, vol. 419, No. 1, pp. 339-346, Aug. 2, 2011.

EPO, Extended European search report of the corresponding European Patent Application No. 19739175.8, dated Feb. 17, 2022.

* cited by examiner

DRUG AND LAYERED SILICATE COMPOSITE WITH IMPROVED ORAL BIOAVAILABILITY, ORAL PHARMACOLOGICAL COMPOSITION CONTAINING THE COMPOSITE AND METHOD FOR PRODUCING THE COMPOSITE

BACKGROUND

Field

The present disclosure relates to a drug and layered silicate composite in which sorafenib as an oral anticancer drug with a low solubility and poor absorption into a body is absorbed onto a layered silicate having a wide reaction surface area, thereby improving eruption in an intestine and oral bioavailability of the sorafenib, to an oral pharmacological composition containing the composite, and to a method for producing the drug and layered silicate composite.

Description of Related Art

In order for a drug to be administered orally to have a sufficient pharmacological effect in the body, the drug should be properly absorbed through a gastrointestinal tract to a target portion to exhibit a drug effect with high bioavailability. In order for the drug to be absorbed to the target portion, the drug must be sufficiently dissolved and erupted in the gastrointestinal tract and the erupted drug molecules must be able to penetrate an intestinal membrane. However, a poorly soluble drug has a low bioavailability due to insufficient eruption in the gastrointestinal tract.

Sorafenib as an oral anticancer drug has an anticancer efficacy because it has a targeting ability to cancer cells. Sorafenib is used for liver cancer, kidney cancer, thyroid cancer and the like. Sorafenib is highly permeable to the intestinal membrane, but its solubility is so low that the oral bioavailability is low and its stability at a room temperature is low. In this connection, a tosylate salt in combination with the sorafenib has been used to improve the drug stability, but the solubility of the drug is still very low.

Sorafenib is currently marketed by Bayer company under the name Nexavar and is intended to be taken twice daily. In vivo half-life of the drug is very long, that is, about 1-2 days. However, because a target absorption of the drug into the target portion is not achieved by one dose, the drug may reach a steady-state in a blood about a week after taking the drug orally. More than 70% of an amount of the drug taken during this duration are known to be excreted in feces, thus leading to a high ratio of drug loss.

Therefore, it is very important to improve the solubility and eruption properties of the insoluble drug such as sorafenib in the gastrointestinal tract in order to improve the absorption of such an insoluble drug. Because sorafenib is highly permeable to the gastrointestinal tract, improving the solubility and eruption properties thereof may allow sufficient absorption improvement and high bioavailability to be achieved. Further, when a blood concentration of sorafenib reaches a target effective concentration, shortening of the treatment period of patients may also be expected.

Conventionally, in order to improve absorption of an insoluble drug, a method of applying a drug in a dissolved state using a co-solvent or emulsion has been proposed. However, this method requires use of a large amount of organic solvents and surfactants necessary for dissolving the poorly soluble drug, which may lead to toxicity and side effects to the gastrointestinal tract. Further, when the co-solvent or emulsion is diluted in the gastrointestinal tract, the drug may not be erupted again therein due to recrystallization and sedimentation of the insoluble drug resulting from a decrease in solubility thereof.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a sorafenib and layered silicate composite that can improve the eruption and bioavailability of the sorafenib as an insoluble drug.

Another purpose of the present disclosure is to provide an oral pharmacological composition containing the sorafenib and layered silicate composite.

Still another purpose of the present disclosure is to provide a method for producing the sorafenib and layered silicate composite.

In a first aspect of the present disclosure, there is provided a drug and layered silicate composite comprising: layered silicate powders; and a drug compound bound to between layers of the silicate powders, wherein the drug compound is present in an amorphous state in the composite.

In one embodiment of the first aspect, the drug compound includes a sorafenib compound or a salt compound containing the sorafenib compound.

In one embodiment of the first aspect, the layered silicate powder includes at least one selected from a group consisting of bentonite, illite, beidelite, hectorite, glauconite, nontronite, and saponite.

In one embodiment of the first aspect, the drug and layered silicate composite contains about 5 to 50% by weight of the drug compound and about 50 to 95% by weight of the layered silicate powders.

In a second aspect of the present disclosure, there is provided an oral pharmacological composition containing: drug and layered silicate composite powders, wherein the composite powders comprises: layered silicate powders; and a drug compound bound to between layers of the silicate powders, wherein the drug compound is present in an amorphous state in the composite powders; and an additive to control uniform distribution of the composite powders in a gastrointestinal tract or to control a release rate of the drug compound in the gastrointestinal tract.

In one embodiment of the second aspect, the composite powders are encapsulated in a hard capsule, wherein a disintegrant, an excipient, a release-sustaining agent or a lubricant is received in the capsule.

In one embodiment of the second aspect, the additive includes at least one selected from a group consisting of polyethylene glycol, polyvinylpyrrolidone, Tween, poloxamer, Solutol HS15, phosphatidylcholine, hydroxypropylmethylcellulose, eudragit, lactose and sorbitol.

In a third aspect of the present disclosure, there is provided a method for producing a drug and layered silicate composite, the method comprising: producing a drug solution by dissolving a drug compound containing sorafenib in an organic solvent; producing a silicate dispersion by dispersing layered silicate powders in an acidic hydrophilic solvent; and mixing the drug solution with the silicate dispersion to bind molecules of the drug compound to the layered silicate powders to form the drug and layered silicate composite.

In one embodiment of the third aspect, the hydrophilic solvent includes an acidic aqueous solution of pH 5 or lower.

In one embodiment of the third aspect, the hydrophilic solvent includes at least one selected from a group consisting of hydrochloric acid, phosphoric acid, sulfuric acid, acetic acid and formic acid.

In one embodiment of the third aspect, the organic solvent includes at least one selected from a group consisting of methanol, ethanol, propanol, acetone, acetonitrile, butanediol, diethanolamine, formamide, dimethylformamide, dimethylsulfoxide, dimethylacetamide, glycerol, tetrahydrofuran, and propylene glycol.

In one embodiment of the third aspect, a concentration of the drug compound in the drug solution is in a range of about 0.1 mg/mL inclusive and about 50 mg/mL inclusive, wherein a concentration of the layered silicate powders in the silicate dispersion is in a range of about 0.1 mg/mL inclusive and about 50 mg/mL inclusive, wherein a content of the organic solvent in a mixed solution of the drug solution and the silicate dispersion is in a range of from 1 volume % inclusive to 40 volume % inclusive.

In one embodiment of the third aspect, the content of the organic solvent in the mixed solution of the drug solution and the silicate dispersion is in a range of from 17 volume % inclusive to 25 volume % inclusive.

In one embodiment of the third aspect, a weight of the silicate powders in the mixed solution is at least three times of a weight of the drug compound.

In one embodiment of the third aspect, the method further comprises, after mixing the drug solution with the silicate dispersion to form a mixed solution, centrifuging the mixed solution to remove supernatant therefrom.

In one embodiment of the third aspect, the method further comprises washing the drug and layered silicate composite using water or the hydrophilic solvent.

In one embodiment of the third aspect, the method further comprises lyophilizing the drug and layered silicate composite.

In one embodiment of the third aspect, the method further comprises lyophilizing the drug and layered silicate composite.

According to the present disclosure, the binding of the insoluble drug such as sorafenib to the layered silicate on a molecule basis may facilitate uniform dispersion of the very hydrophobic drug in water, and may allow an eruption rate of the drug in the gastrointestinal tract to be significantly increased. Further, the in vivo absorption and oral bioavailability of the drug through the oral administration may be significantly improved, which can contribute to a rapid achievement of a target in-blood drug concentration, improvement of a therapeutic effect and prevention of unnecessary drug loss. Moreover, improving the bioavailability may allow reducing an amount of the drug needed to achieve the same therapeutic effect.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "substantially," "about," and similar terms are used as terms of approximation and not as terms of degree, and are intended to account for the inherent deviations in measured or calculated values that would be recognized by those of ordinary skill in the art. The term may be used to prevent unauthorized exploitation by an unauthorized infringer to design around accurate or absolute figures provided to help understand the present disclosure.

A drug and layered silicate composite according to embodiments of the present disclosure includes a layered silicate and a drug compound adsorbed to the layered silicate.

The layered silicate may be in the form of fine powders, and may have a structure in which plate-like structures are laminated in which each plate-like structure is made of combination of metal ions such as aluminum (Al), sodium (Na) and calcium (Ca) and silicic acid. In one embodiment, the layered silicate may be fine powders of clay minerals containing at least about 50% by weight of montmorillonite relative to the total weight thereof. For example, the layered silicate may include one or more selected from a group consisting of bentonite, illite, beidelite, hectorite, glauconite, nontronite, saponite and the like.

The drug compound may include a sorafenib compound. The drug compound may be a compound of sorafenib alone having a following Chemical Formula 1. Alternatively, the drug compound may be a salt compound in which sorafenib and an anionic compound are combined to each other, such as a sorafenib tosylate compound of Chemical Formula 2 below. In one embodiment, the drug compound may be ionically bound to the layered silicate. Alternatively, the drug compound may be physically adsorbed to the layered silicate.

[Chemical Formula 1]

[Chemical Formula 2]

In one embodiment, the drug and layered silicate composite may contain about 5 to 50% by weight of the drug compound and about 50 to 95% by weight of the layered silicate based on a total weight of the composite. When the content of the drug compound is smaller than 5% by weight, the amount of the composite to be taken by a patient to administer the same drug amount into a target portion may be excessively increased. When the content of the drug compound exceeds 50% by weight, the amount of drug compound lost in a process of producing the composite may be increased. For example, the content of the drug compound in the drug and layered silicate composite may be in a range of about 20 to 30% by weight.

In one embodiment, the drug compound bound to the layered silicate may be in an amorphous state.

An oral pharmacological composition according to an embodiment of the present disclosure may contain the drug and layered silicate composite powders and additives.

The additive may control a drug uniform dispersion or a drug release rate of the drug-silicate composite powders in the gastrointestinal tract and may include surfactants, solubilizers, and excipients. For example, the additives may include one or more selected from polyethylene glycol, polyvinylpyrrolidone, Tween, poloxamer, Solutol HS15, phosphatidylcholine, hydroxypropylmethylcellulose, eudragit, lactose, sorbitol, etc.

The drug and layered silicate composite powders may be mixed directly with the additive. Alternatively, the drug and layered silicate composite powders may be mixed with the surfactant so as to be sealed in a hard capsule, for example, a tablet. When the drug and layered silicate composite powders are encapsulated in hard capsules, disintegrants, excipients, release-sustaining agents, lubricants, etc. may be added into the hard capsules to aid the release and disintegration of the drug.

Figure 1:
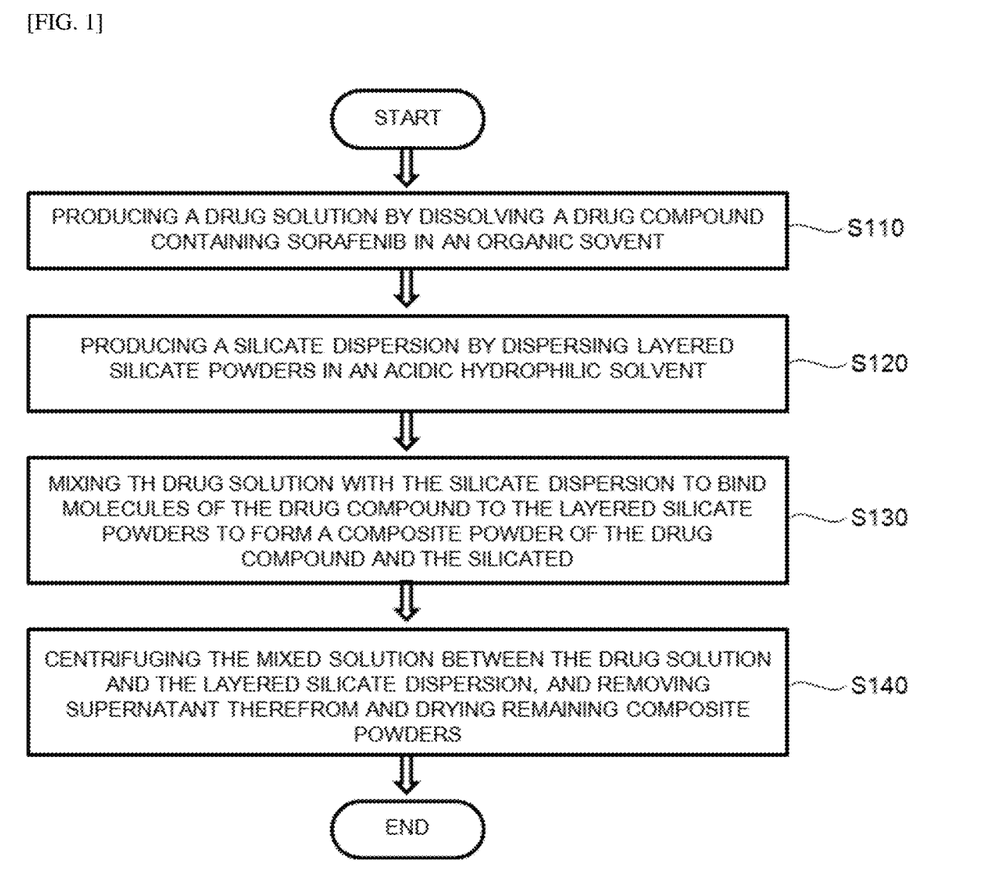
FIG. 1 is a flow chart illustrating a method for producing a drug and layered silicate composite according to an embodiment of the present disclosure.

FIG. 1 is a flow chart illustrating a method for producing a drug and layered silicate composite according to an embodiment of the present disclosure.

Referring to FIG. 1, a method for producing a drug and layered silicate composite according to an embodiment of the present disclosure includes a first step S110 of preparing a drug solution by dissolving a drug compound including sorafenib in an organic solvent; a second step S120 of dispersing layered silicate powders in an acidic hydrophilic solvent to produce a silicate dispersion; and a third step S130 of mixing the drug solution with the silicate dispersion to bind the drug compound to the layered silicate powders.

In the first step S110, the organic solvent may be mixed with the hydrophilic solvent of the silicate dispersion while dissolving the drug including the sorafenib. Examples of the organic solvent may include methanol, ethanol, propanol, acetone, acetonitrile, butanediol, diethanolamine, formamide, dimethylformamide, dimethylsulfoxide, dimethylacetamide, glycerol, tetrahydrofuran, propylene glycol, etc. which may be used alone or in a mixture of two or more.

In one embodiment, in the drug solution, the concentration of the drug compound may be in a range of about 0.1 to 50 mg/mL.

In the second step S120, an acidic aqueous solution may be used as the hydrophilic solvent. When the acidic aqueous solution is used as the hydrophilic solvent, the acidic aqueous solution may ionize the drug compound molecule with an amine group to improve the solubility of the drug compound in a mixed solvent of the hydrophilic solvent and the organic solvent. Further, the acidic aqueous solution may allow binding of the drug compound to the surface or interlayers of negatively charged layered silicate powders to be improved.

It is desirable that the hydrophilic solvent has a pH condition that may ionize the drug compound without decomposing the drug compound. For example, an acidic aqueous solution having a pH of about 5 or lower, preferably an acidic aqueous solution having a pH of about 1 to 5 may be used as the hydrophilic solvent. For example, the hydrophilic solvent may include a hydrochloric acid solution, a phosphoric acid solution, a sulfuric acid aqueous solution, an acetic acid aqueous solution, or a formic acid aqueous solution, or a mixture of two or more thereof.

In one embodiment, in the silicate dispersion, the concentration of the layered silicate powders may be in a range of about 0.1 to 50 mg/mL.

In the third step 130, a content ratio of the organic solvent in the mixed solvent of the hydrophilic solvent and the organic solvent may be in a range of about 1 to 40% by volume. When the proportion of the organic solvent is smaller than 1% by volume, the solubility of the drug compound may be lowered. When the proportion of the organic solvent exceeds 40% by volume, the binding effect of the drug compound on the layered silicate may be significantly reduced and thus the yield of the composite may be reduced. In one embodiment, the content ratio of the organic solvent in the mixed solvent of the hydrophilic solvent and the organic solvent may be in a range of from 17 to 25% by volume.

In order to minimize the phenomenon that the drug compound is incompletely dissolved or is precipitated during reaction in the production of the drug and layered silicate composite powders, it is preferable to completely dissolve the drug compound in the organic solvent to form the mixture solution and then mix the mixture solution with the layered silicate dispersion.

In one example, the amount of the drug compound that can bind to the layered silicate powders is limited. Thus, it is desirable to set the mixing ratio of the silicate powders and the drug compound in the mixed solution, with considering the content of the drug compound in the drug and layered silicate composite powders and a percentage of the drug compound that is not bound to the layered silicate powders.

In one embodiment, the weight of the silicate powders in the mixed solution may be in a range of from about 2.5 times to about 10 times of the weight of the drug compound. When the weight of the layered silicate powders is smaller than 2.5 times of the weight of the drug compound, the ratio of the drug compound binding to the silicate powders may be reduced, resulting in increased loss of the drug compound. When the weight of the layered silicate powders exceeds 10 times of the weight of the drug compound, the content of the drug compound contained in the composite is too low, thereby to cause an excessive increase in the amount of the composite to be taken by a patient to administer the same drug amount into the target portion of the patient body. For example, the weight of the bentonite powders may be preferably about 3 times or larger and about 5 times or smaller than that of the drug compound.

The method for producing a drug and layered silicate composite according to an embodiment of the present disclosure may further include a fourth step S140 of centrifuging the mixed solution of the drug solution and the layered silicate dispersion, and removing supernatant therefrom and drying remaining composite powders.

The drug and layered silicate composite powders formed after mixing the drug solution with the layered silicate dispersion may be dispersed or precipitated in the mixed solvent. A portion of the drug compound may be not adsorbed to the layered silicate powders and may be present in a dissolved form in the mixed solvent.

Centrifuging this mixed solution may allow the produced drug and layered silicate composite powders to be settled down. Further, removing the supernatant after the centrifugation may allow the drug compound remaining in the solvent and not binding to the layered silicate powders to be removed.

In one example, the method for producing a drug and layered silicate composite according to an embodiment of the present disclosure may further include washing and purifying the produced drug and layered silicate composite powders using water or a hydrophilic solvent to remove the residual solvent or the remaining drug compound in a dissolved state after the centrifugation. After the purification, the drug and layered silicate composite powders may be lyophilized.

The drug and layered silicate composite thus produced may be administered directly orally to the patient in the form of powders, or may be administered indirectly and orally in the form of hard capsules or tablets. In this regard, the disintegrants, excipients, release-sustaining agents, lubricants and the like may be added to the hard capsule or tablet to aid release and disintegration of the drug.

Hereinafter, some Present Examples and Experimental Examples in the present disclosure will be described in detail. However, the following Present Examples are only some embodiments of the present disclosure, and the scope of the present disclosure should not be interpreted as being limited to the Present Examples.

Present Examples 1 to 4

Sorafenib was completely dissolved in dimethyl sulfoxide to produce a 25 mg/mL concentration of the drug solution. Then, bentonite powders were dispersed in 1 N aqueous hydrochloric acid solution to produce bentonite dispersion at a concentration of 5 mg/mL. Subsequently, 0.2 mL of the drug solution was mixed with acetonitrile and 5 mL of the bentonite dispersion. Then, 1 N hydrochloric acid was further added thereto to reach a total volume of 10 mL. In this connection, 1.5 mL of acetonitrile was mixed in Present Example 1; 2 mL of acetonitrile was mixed in Present Example 2; in Present Example 3, 3 mL of acetonitrile was mixed; and in Present Example 4, 4 mL of acetonitrile was mixed.

Subsequently, the mixed solution was homogeneously mixed and left for 30 minutes to bind the drug compound to the bentonite powders.

Table 1 below shows amounts of drug compounds and bentonite as used and compositions of solvents according to Present Examples 1 to 4.

TABLE 1

| Present Example | Sorafenib (mg) | Bentonite (mg) | Dimethyl sulfoxide (mL) | Acetonitrile (mL) | 1N HCl (mL) |
|---|---|---|---|---|---|
| 1 | 5 | 25 | 0.2 | 1.5 | 8.3 |
| 2 | 5 | 25 | 0.2 | 2 | 7.8 |
| 3 | 5 | 25 | 0.2 | 3 | 6.8 |
| 4 | 5 | 25 | 0.2 | 4 | 5.8 |

Experimental Example 1

The reaction-terminated mixture solution was centrifuged at a speed of 3,000 rpm for 5 minutes, and, then, the amount of the drug compound contained in the supernatant was measured. Subtracting the amount of the drug compound contained in the supernatant from the total amount of the drug compound used may allow the amount of the drug bound to the bentonite powders to be calculated. Thus, a ratio of the adsorbed drug compound among the entire drug compound was calculated.

Table 2 below shows binding ratios of the sorafenib to the bentonite powders in Present Examples 1 to 4.

TABLE 2

| Present Example | Binding ratio (%) |
|---|---|
| 1 | 98.1 ± 0.1 |
| 2 | 95.3 ± 0.1 |
| 3 | 66.6 ± 0.2 |
| 4 | 6.0 ± 1.0 |

Table 1 and Table 2 showed that as the content of the organic solvent acetonitrile increases in the mixed solvent, the binding ratio of sorafenib to the bentonite powders decreased rapidly. Specifically, in Present Examples 1 and 2 where the content of the organic solvent in the mixed solvent were 17 vol % and 22 vol % respectively, the binding ratios were about 98.1% and 95.3%, respectively. Present Examples 3 and 4, which contained 32 vol % and 42 vol % organic solvents in the mixed solvent respectively showed about 66.6% and 6% binding ratios respectively.

In one example, the solubility of sorafenib when the ratio between acetonitrile and 1 N hydrochloric acid was adjusted while the dimethyl sulfoxide ratio in the total mixed solvent was fixed at 2% was measured. As a result, we dissolved the sorafenib at a concentration of 0.5 mg/mL while at a concentration of 15% acetonitrile and 83% of 1 N hydrochloric acid.

Therefore, in consideration of the binding ratio and solubility of the drug compound, the ratio of the organic solvent in the mixed solvent is preferably about 17% by volume or larger and about 25% by volume or smaller.

Present Examples 5 to 8

While the amount of sorafenib as used, the solvent composition and the production condition were the same as those in Present Example 1, and the amount of bentonite as used varied, the composite was produced.

Table 3 below shows the amounts of the drug compound and bentonite as used and the compositions of solvents according to Present Example 1 and Present Examples 5 to 8.

TABLE 3

| Present Example | Sorafenib (mg) | Bentonite (mg) | Dimethyl sulfoxide (mL) | Acetonitrile (mL) | 1N HCl (mL) |
|---|---|---|---|---|---|
| 5 | 5 | 5 | 0.2 | 1.5 | 8.3 |
| 6 | 5 | 10 | 0.2 | 1.5 | 8.3 |
| 7 | 5 | 15 | 0.2 | 1.5 | 8.3 |
| 1 | 5 | 25 | 0.2 | 1.5 | 8.3 |
| 8 | 5 | 50 | 0.2 | 1.5 | 8.3 |

Experimental Example 2

The reaction-terminated mixture solution was centrifuged at a speed of 3,000 rpm for 5 minutes, and, then, the amount of the drug compound contained in the supernatant was measured. Subtracting the amount of the drug compound contained in the supernatant from the total amount of the drug compound used may allow the amount of the drug bound to the bentonite powders to be calculated. Thus, a ratio of the adsorbed drug compound among the entire drug compound was calculated.

Table 4 below shows binding ratios of the sorafenib to the bentonite powders in Present Example 1 and Present Examples 5 to 8.

TABLE 4

| Present Example | Binding ratio (%) |
|---|---|
| 5 | 61.2 ± 1.3 |
| 6 | 86.6 ± 0.4 |
| 7 | 95.6 ± 0.0 |
| 1 | 98.1 ± 0.1 |
| 8 | 98.7 ± 0.0 |

Table 3 and Table 4 showed that as the content of the bentonite powders increases, the binding ratio of the drug compound to the bentonite powders increases. However, when the weight of the bentonite powders is smaller than three times of that of the drug compound, the binding ratio increased rapidly. When the weight of the bentonite powders is larger than three times of that of the drug compound, the increase rate of the binding ratio decreased sharply. Further, when the weight of the bentonite powders is larger than three times of that of the drug compound, more than 95% of the drug compound was found to bind to the bentonite powders.

It may be seen from the above findings that in mixing of the bentonite powders and drug compound to produce the composite therebetween, the weight of the bentonite powders is preferably about 2.5 to 10 times that of the drug compound. More preferably, the weight of the bentonite powders is about 3 times or larger and about 5 times or smaller that of the drug compound.

Experimental Example 3

Physical properties of the products were evaluated based on selected compositions. Sorafenib was adsorbed on the bentonite powders for 30 minutes according to Present Example 7 to form a mixture. The mixture was centrifuged at 3,000 rpm for 5 minutes, and supernatant was removed therefrom. 0.1 N hydrochloric acid was added to the submerged composite to re-disperse the composite. Then, second supernatant was removed by centrifugation and remaining organic solvent was removed as much as possible.

Remaining precipitates were then lyophilized to obtain drug and bentonite composite powders.

A mass of the obtained drug-bentonite composite powders was measured. Then, a ratio of a yield of the composite powder as a mass of the resulting composite powders to the total mass of the initial drug compound and bentonite powders was calculated. The ratio was calculated as about 85.1±2.7%. Subsequently, a certain amount of the composite was suspended in phosphate buffered saline (pH 7.4), and then the suspension was diluted with acetonitrile. Then, the drug was extracted. Thus, the drug content in the composite was calculated to be about 25.0±0.7%.

Experimental Example 4

SEM was used to confirm the morphological characteristics of the drug and bentonite composite. To this end, the sorafenib compound, and the sorafenib and bentonite composite powders produced according to Present Example 7 were respectively adhered to a copper tape and were subjected to platinum coating at 30 mA for 200 seconds.

Figure 2:
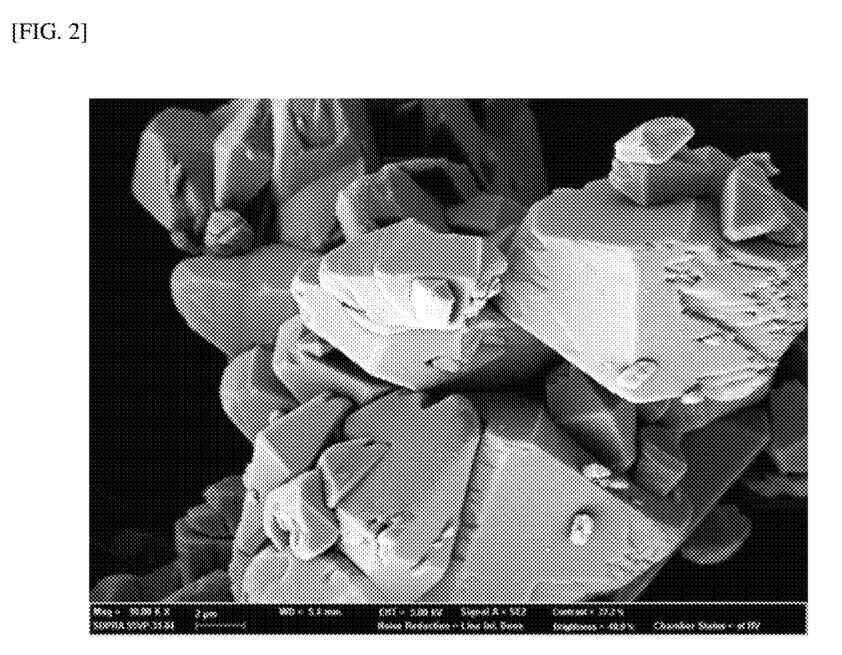
FIG. 2 and FIG. 3 show scanning electron microscopy (SEM) images of surfaces of sorafenib compound and sorafenib and bentonite composite powders after platinum coating thereon.
Figure 3:
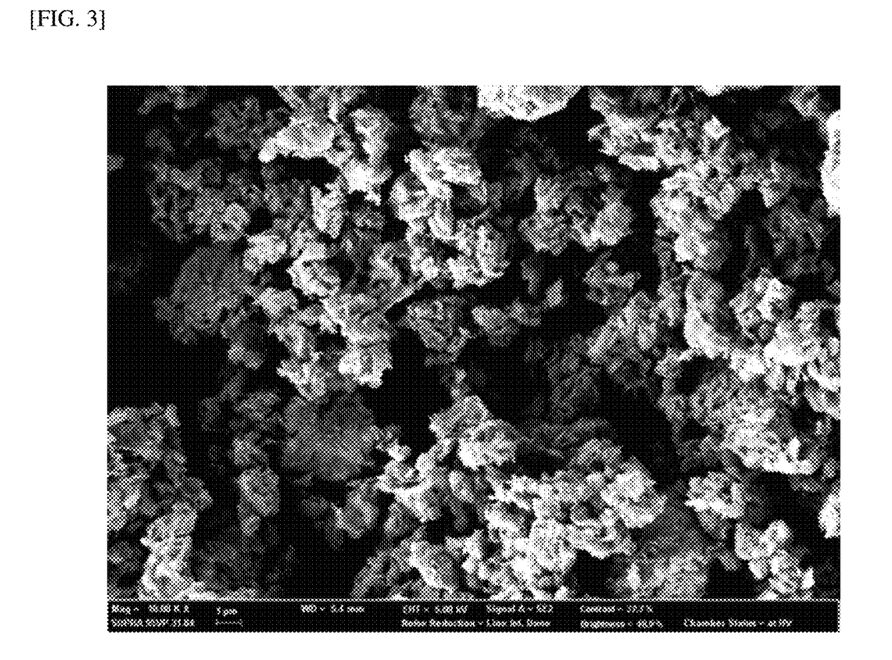

FIG. 2 and FIG. 3 show scanning electron microscopy (SEM) images of surfaces of sorafenib compound and sorafenib and bentonite composite powders after platinum coating thereon.

FIG. 2 and FIG. 3 show that using the sorafenib compound, a crystal size of greater than or equal to 10 μm occurred, whereas, using the sorafenib and bentonite composite powders, only a bentonite structure with an irregular shape appeared without such a large crystal structure.

Experimental Example 5

A crystal structure of the drug before and after the adsorption thereof to the bentonite was confirmed by a X-ray diffraction (XRD) analysis. The sorafenib, the bentonite, a physical mixture of the sorafenib and bentonite, and the sorafenib and bentonite composite were subjected to the X-ray diffraction (XRD) analysis where the 2 theta range was set to 3 to 45°.

Figure 4:
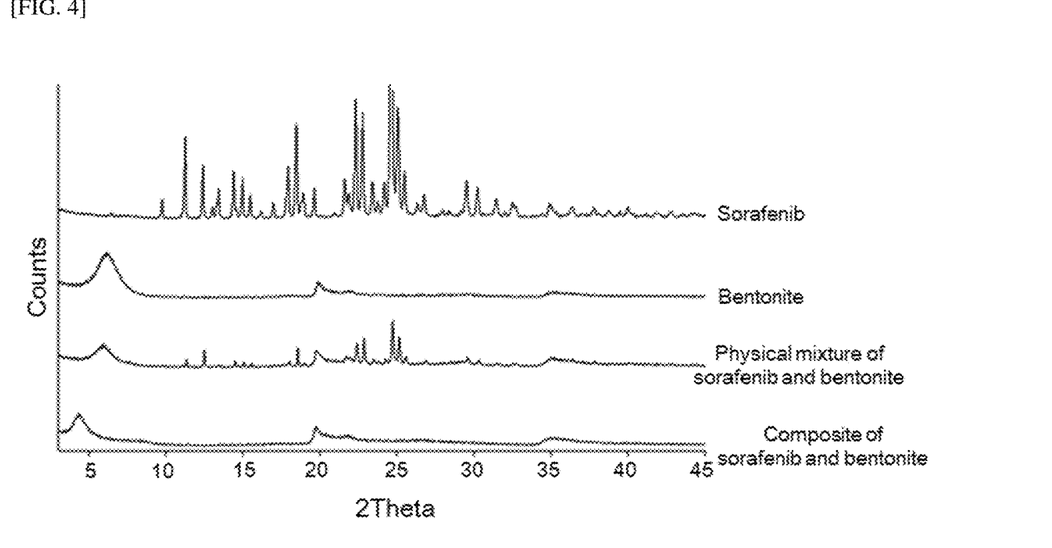
FIG. 4 shows a X-ray diffraction (XRD) analysis result of sorafenib, bentonite, a physical mixture of sorafenib and bentonite, and a sorafenib and bentonite composite.

FIG. 4 shows a X-ray diffraction (XRD) analysis result of sorafenib, bentonite, a physical mixture of sorafenib and bentonite, and a sorafenib and bentonite composite. FIG. 4 shows that an inherent XRD pattern or peak of the sorafenib appeared in a portion of the physical mixture of sorafenib and bentonite, while the inherent XRD pattern or peak of the sorafenib was not present in the sorafenib and bentonite composite. These results show that the sorafenib bound to the bentonite is present in an amorphous state.

Experimental Example 6

Drug release experiments were conducted to confirm the release of the drug from the bentonite based on the surrounding environment type. Specifically, the sorafenib 800 μg and the bentonite composite produced under the process condition of Present Example 7 containing 800 μg of sorafenib were dispersed in 40 ml of an eruption solution respectively to form two dispersions. The, each dispersion was shaken at 37° C. at 50 rpm to effect eruption.

The eruption solution used in this experiment was embodied as each of a solution of 0.1 N HCl in water at pH 1.2 and 50 mM phosphate buffer at pH 7.4. Further, 0.5% (v/v) Tween 80 (Polyoxyethyelene Sorbitan Monooleate) was added to the eruption solution to dissolve the sorafenib sufficiently.

Then, the eruption solution was collected based on a time schedule by 0.4 mL, filtered and analyzed by a high performance liquid chromatography.

Figure 5:
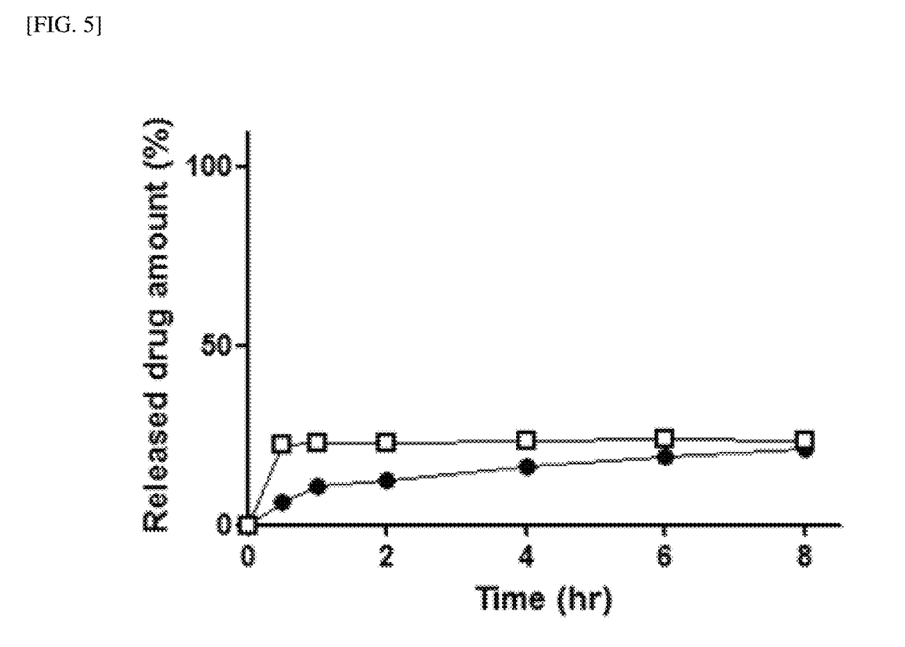
FIG. 5 is a graph showing drug release patterns of sorafenib (●) and a sorafenib and bentonite composite (□) in 0.1 N HCl aqueous solution at pH 1.2.
Figure 6:
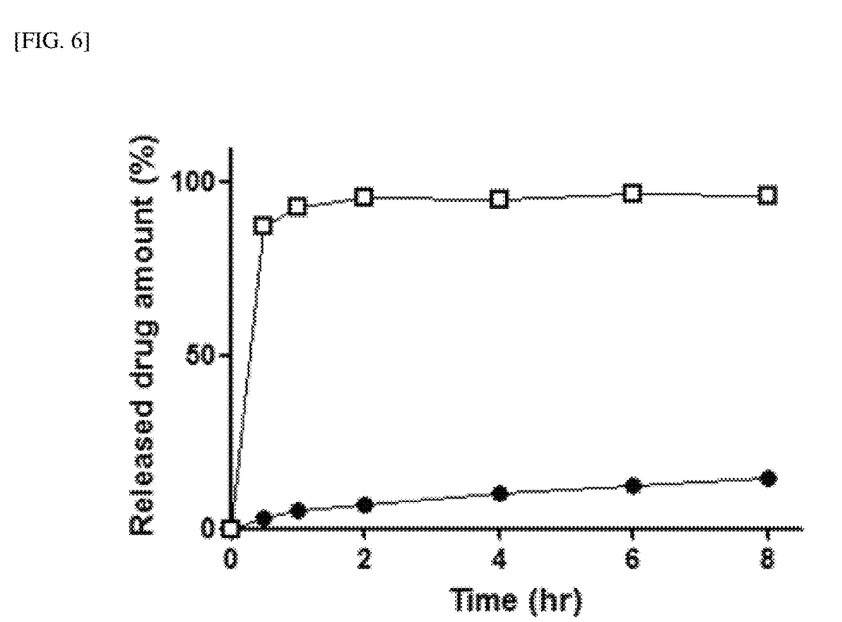
FIG. 6 is a graph showing drug release patterns of sorafenib (●) and a sorafenib and bentonite composite (□) in 50 mM phosphate buffer at pH 7.4.

FIG. 5 is a graph showing drug release patterns of sorafenib (●) and a sorafenib and bentonite composite (□) in 0.1 N HCl aqueous solution at pH 1.2. FIG. 6 is a graph showing drug release patterns of sorafenib (●) and a sorafenib and bentonite composite (□) in 50 mM phosphate buffer at pH 7.4.

FIG. 5 and FIG. 6 showed that when using the sorafenib alone, the sorafenib is relatively fast erupted in the solution of 0.1 N HCl at pH 1.2 than in 50 mM phosphate buffer at pH 7.4. However, FIG. 5 and FIG. 6 showed that when using the sorafenib alone, the released amount of the sorafenib reaches a value below 30% for 8 hours and thus the release rate was very low in both of the solutions of 0.1 N HCl at pH 1.2 and 50 mM phosphate buffer at pH 7.4.

On the other hand, FIG. 5 and FIG. 6 showed that when using the sorafenib and bentonite composite, the released amount of the sorafenib reaches about 25% and thus the release rate was low in the solution of 0.1 N HCl at pH 1.2, whereas almost all of the drug was released in a short time in 50 mM phosphate buffer at pH 7.4.

These results suggest that binding of the sorafenib to the bentonite may allow the drug release rate to increase in a neutral pH environment as in the lower digestive tract.

Experimental Example 7

In order to evaluate the absorption and disappearance rate of the drug during oral administration, a in vivo pharmacokinetics analysis was performed on rats. A femoral artery of the rat was cannulated with PESO tubes. Then, sorafenib suspension, and sorafenib and bentonite composite suspension as produced according to Present Example 7 were orally administered into the rat. Thereafter, the rat blood was collected through the PESO tube based on a time schedule and was centrifuged to obtain plasma. After the plasma samples were pretreated, the in-blood drug concentration was analyzed using a mass spectrometer. The dose was set to 10 mg/kg based on the amount of the sorafenib. The plasma was collected over 2 days.

Figure 7:
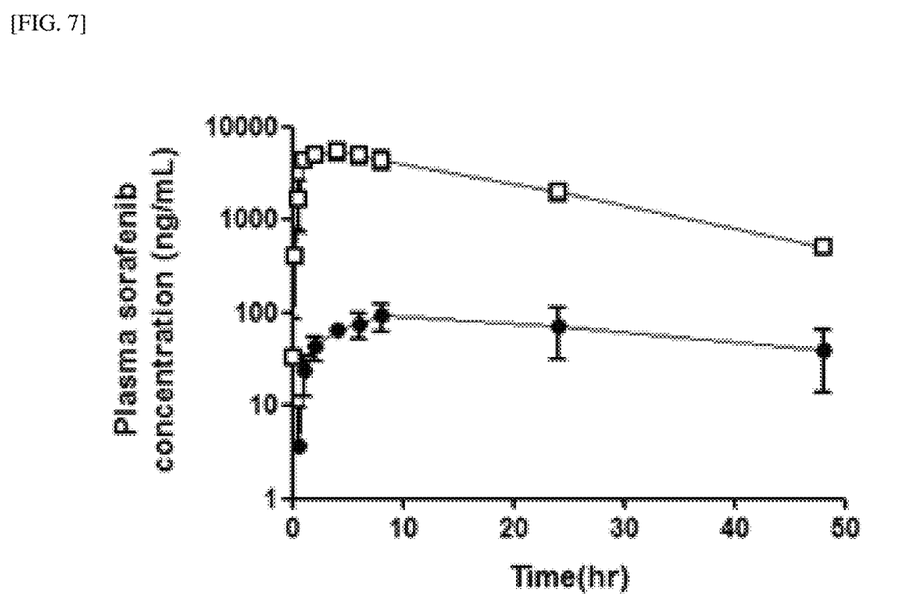
FIG. 7 is a graph showing changes in concentration of a drug in a blood over time in oral administration of sorafenib suspension (●) and sorafenib and bentonite composite suspension (□).

FIG. 7 is a graph showing changes in concentration of a drug in a blood over time in oral administration of sorafenib suspension (●) and sorafenib and bentonite composite suspension (□). Table 5 below shows pharmacokinetics parameters as calculated based on the relevant in-blood drug concentration data.

FIG. 7 and Table 5 showed that an in-blood drug concentration was significantly higher when the sorafenib and bentonite composite suspension was orally administered, compared to when the sorafenib suspension was orally administered. FIG. 7 and Table 5 further showed that a maximum in-blood drug concentration (Cmax) and AUC (area under the in-blood drug concentration curve) as calculated based on the results of the in-blood drug concentration analysis were also higher when the sorafenib and bentonite composite suspension was administered orally than when the sorafenib suspension was orally administered.

These results suggest that when the sorafenib as an insoluble drug binds to the bentonite and then the sorafenib-bound bentonite is administered orally, the drug sorafenib absorption and bioavailability could be improved compared to when the sorafenib only is orally administered.

TABLE 5

| Pharmacokinetics | Sorafenib powders | Sorafenib and bentonite composite powders |
|---|---|---|
| $C_{max}$ (μg/mL) | 0.10 ± 0.02 | 5.41 ± 1.03 |
| $T_{max}$ (min) | 400 ± 69.3 | 200 ± 69.3 |
| $AUC_{last}$ (μg · min/mL) | 187.13 ± 78.39 | 7065.79 ± 1308.90 |
| $AUC_{inf}$ (μg · min/mL) | 291.03 ± 157.87 | 7622.86 ± 1379.46 |
| $t_{1/2}$ (min) | 1692.5 ± 368.8 | 767.2 ± 22.1 |
| MRT (min) | 1228.9 ± 138.7 | 859.13 ± 21.2 |
| Relative bioavailability (%) | — | 2619.2 |

According to the present disclosure, the binding of the insoluble drug such as sorafenib to the layered silicate on a molecule basis may facilitate uniform dispersion of the very hydrophobic drug in water, and may allow an eruption rate of the drug in the gastrointestinal tract to be significantly increased. Further, the in vivo absorption and oral bioavailability of the drug through the oral administration may be significantly improved, which can contribute to a rapid achievement of a target in-blood drug concentration, improvement of a therapeutic effect and prevention of unnecessary drug loss. Moreover, improving the bioavailability may allow reducing an amount of the drug needed to achieve the same therapeutic effect.

The illustrations of the presented embodiments are provided so that a person of ordinary skill in the art of the present disclosure may use or implement the present disclosure. Various modifications to these embodiments will be readily apparent to those skilled in the art of the present disclosure. The general principles defined herein may be applied to other embodiments without departing from the scope of the present disclosure. Thus, the present disclosure is not to be construed as limited to the embodiments set forth herein but rather to be accorded the widest scope consistent with the principles and novel features set forth herein.

What is claimed is:

1. A drug and layered silicate composite comprising: layered silicate powders comprising bentonite; and a drug compound bound to between layers of the silicate powders, wherein the drug compound is present in an amorphous state in the composite, wherein a weight of the bentonite is 3 to 5 times a weight of the drug compound, wherein the drug compound includes a sorafenib compound or a salt compound containing the sorafenib compound, wherein the drug and layered silicate composite has a greater release amount and release rate of the drug compound in pH 7.4 buffer than pH 1.2 aqueous solution, wherein the release amount of the drug compound is 2 times or more in the pH 7.4 buffer than in the pH 1.2 aqueous solution.

2. An oral pharmacological composition containing: drug and layered silicate composite powders, wherein the composite powders comprise: layered silicate powders comprising bentonite; and a drug compound bound to between layers of the silicate powders, wherein the drug compound is present in an amorphous state in the composite powders; and an additive to control uniform distribution of the composite powders in a gastrointestinal tract or to control a release rate of the drug compound in the gastrointestinal tract, wherein a weight of the bentonite is 3 to 5 times a weight of the drug compound, wherein the drug compound includes a sorafenib compound or a salt compound containing the sorafenib compound, wherein the drug and layered silicate composite has a greater release amount and release rate of the drug compound in pH 7.4 buffer than pH 1.2 aqueous solution, wherein the release amount of the drug compound is 2 times or more in the pH 7.4 buffer than in the pH 1.2 aqueous solution.

3. The oral pharmacological composition of claim 2, wherein the composite powders are encapsulated in a hard capsule, wherein a disintegrant, an excipient, a release-sustaining agent or a lubricant is received in the capsule.

4. The oral pharmacological composition of claim 2, wherein the additive includes at least one selected from a group consisting of polyethylene glycol, polyvinylpyrrolidone, Tween, poloxamer, Solutol HS15, phosphatidylcholine, hydroxypropylmethylcellulose, eudragit, lactose and sorbitol.

* * * * *